(12) United States Patent
Steinke

(10) Patent No.: US 6,224,626 B1
(45) Date of Patent: *May 1, 2001

(54) ULTRA-THIN EXPANDABLE STENT

(75) Inventor: Tom Steinke, San Diego, CA (US)

(73) Assignee: MD3, Inc., San Diego, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/283,800

(22) Filed: Apr. 1, 1999

Related U.S. Application Data

(63) Continuation-in-part of application No. 09/024,571, filed on Feb. 2, 1998, now Pat. No. 6,033,436.

(51) Int. Cl.⁷ .................................................. A61F 2/00
(52) U.S. Cl. ............................................................ 623/1.16
(58) Field of Search ........................ 623/1, 12, 1.15, 623/1.16; 606/108, 192, 195

(56) References Cited

U.S. PATENT DOCUMENTS

| | | |
|---|---|---|
| 3,620,218 | 11/1971 | Schmitt . |
| 4,553,545 | 11/1985 | Maass et al. . |
| 4,733,665 | 3/1988 | Palmaz . |
| 4,739,762 | 4/1988 | Palmaz . |
| 4,776,337 | 10/1988 | Palmaz . |
| 4,922,905 | 5/1990 | Strecker . |
| 5,059,211 | 10/1991 | Stack et al. . |
| 5,192,307 | 3/1993 | Wall . |
| 5,195,984 | 3/1993 | Schatz . |
| 5,266,073 | 11/1993 | Wall . |
| 5,306,286 | 4/1994 | Stack et al. . |
| 5,306,294 | 4/1994 | Winston et al. . |
| 5,397,355 | 3/1995 | Marin et al. . |
| 5,423,885 | 6/1995 | Williams . |
| 5,441,515 | 8/1995 | Khosravi et al. . |
| 5,443,500 | 8/1995 | Sigwart . |
| 5,449,382 | 9/1995 | Dayton . |
| 5,464,450 | 11/1995 | Buscemi et al. . |
| 5,476,508 | 12/1995 | Amstrup . |
| 5,527,337 | 6/1996 | Stack et al. . |
| 5,549,662 | * 8/1996 | Fordenbacher ........................... 623/1 |
| 5,551,954 | 9/1996 | Buscemi et al. . |
| 5,556,413 | 9/1996 | Lam . |
| 5,578,075 | 11/1996 | Dayton . |
| 5,591,223 | 1/1997 | Lock et al. . |
| 5,603,722 | 2/1997 | Phan et al. . |
| 5,618,299 | 4/1997 | Khosravi et al. . |
| 5,629,077 | 5/1997 | Turnlund et al. . |
| 5,632,771 | 5/1997 | Boatman et al. . |

(List continued on next page.)

FOREIGN PATENT DOCUMENTS

| | | |
|---|---|---|
| WO 96/14030 | 5/1996 | (WO) . |
| WO 98/22045 | 5/1998 | (WO) . |
| WO 99/40874 | 8/1999 | (WO) . |

*Primary Examiner*—Bruce Snow
(74) *Attorney, Agent, or Firm*—Knobbe, Martens, Olson & Bear, LLP

(57) ABSTRACT

The present invention provides a lumen support stent for use in an artery or any body lumen. The stent is formed from a plurality of ladder elements having elongated ribs and end rungs affixed to the elongated ribs. The elongated ribs of adjacent ladder elements are slidably engaged by the end rungs of adjacent ladder elements. Sliding of the elongated ribs creates a variable distance between the end rungs of adjacent ladder elements. Consequently, the stent has a first diameter in which the distance between end rungs of adjacent ladder elements is collapsed, and a variable second diameter in which the distance between end rungs of adjacent ladder elements is expanded.

13 Claims, 14 Drawing Sheets

U.S. PATENT DOCUMENTS

| | | |
|---|---|---|
| 5,643,312 | 7/1997 | Fischell et al. . |
| 5,643,314 | 7/1997 | Carpenter et al. . |
| 5,643,339 | 7/1997 | Kavteladze et al. . |
| 5,649,977 * | 7/1997 | Campbell ................................ 623/1 |
| 5,707,387 | 1/1998 | Wijay . |
| 5,725,549 | 3/1998 | Lam . |
| 5,733,328 | 3/1998 | Fordenbacher . |
| 5,735,872 | 4/1998 | Carpenter et al. . |
| 5,741,293 | 4/1998 | Wijay . |
| 5,766,710 | 6/1998 | Turnlund et al. . |
| 5,851,217 | 12/1998 | Wolff et al. . |
| 5,851,231 | 12/1998 | Wolff et al. . |
| 5,876,419 | 3/1999 | Carpenter et al. . |

* cited by examiner

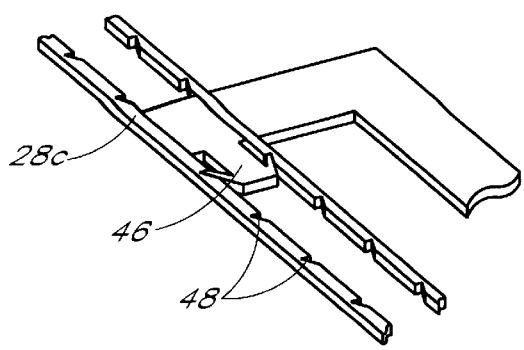
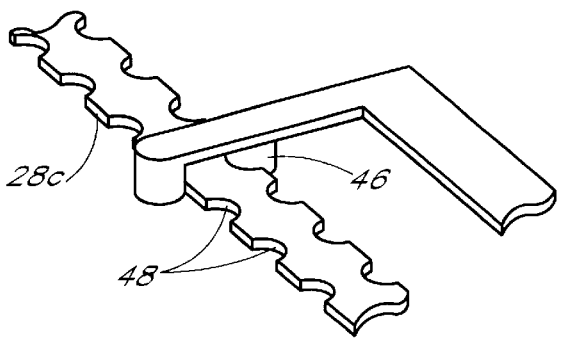
FIG. 17    FIG. 18
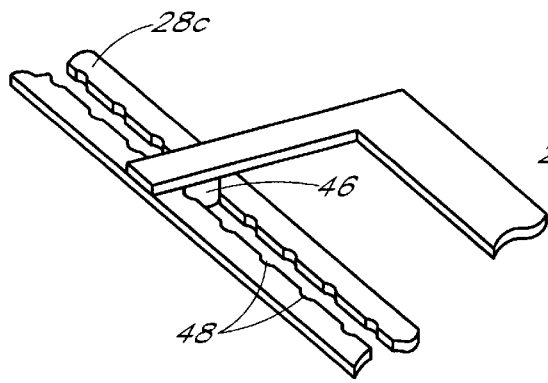
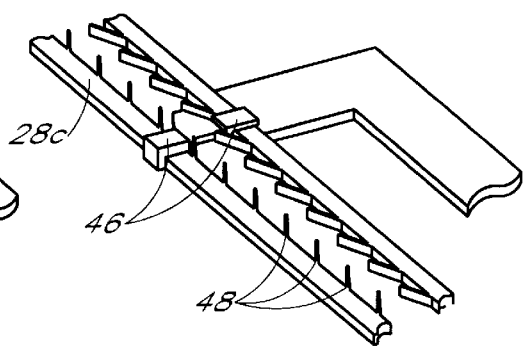
FIG. 19    FIG. 20
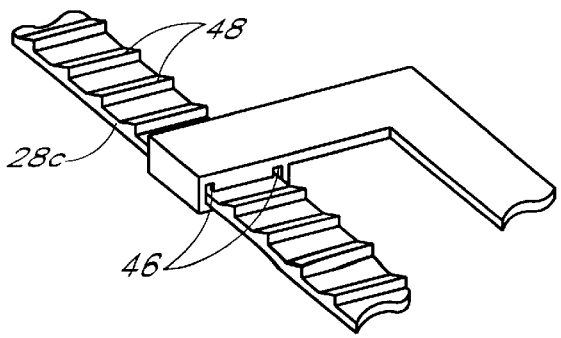
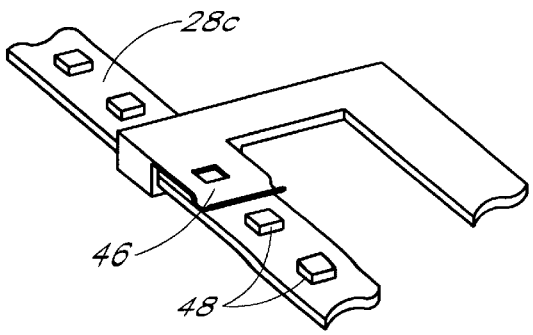
FIG. 21    FIG. 22

ULTRA-THIN EXPANDABLE STENT

RELATED APPLICATIONS

This is a continuation-in-part of pending application Ser. No. 09/024,571, filed on Feb. 2, 1998 now U.S. Pat. No. 6,033,436.

BACKGROUND OF THE INVENTION

This invention relates to expandable medical implants for maintaining support of a body lumen.

An important use of stents is found in situations where part of the vessel wall or stenotic plaque blocks or occludes blood flow in the vessel. Often, a balloon catheter is utilized in a percutaneous transluminal coronary angioplasty procedure to enlarge the occluded portion of the vessel. However, the dilation of the occlusion can cause fissuring of atherosclerotic plaque and damage to the endothelium and underlying smooth muscle cell layer, potentially leading to immediate problems from flap formation or perforations in the vessel wall, as well as long-term problems with restenosis of the dilated vessel. Implantation of stents can provide support for such problems and prevent re-closure of the vessel or provide patch repair for a perforated vessel. Further, the stent may overcome the tendency of diseased vessel walls to collapse, thereby maintaining a more normal flow of blood through that vessel.

Examples of prior developed stents have been described by Balcon et al., "Recommendations on Stent Manufacture, Implantation and Utilization," European Heart Journal (1997), vol. 18, pages 1536–1547, and Phillips, et al., "The Stenter's Notebook," Physician's Press (1998), Birmingham, Mich. The first stent used clinically was the self-expanding "Wallstenf" which comprised a metallic mesh in the form of a Chinese fingercuff. These stents were cut from elongated tubes of wire braid and, accordingly, had the disadvantage that metal prongs from the cutting process remained at the longitudinal ends thereof. The inherent rigidity of the cobalt based alloy with a platinum core used to form the stent together with these terminal prongs made navigation of the blood vessels to the locus of the lesion difficult as well as risky from the standpoint of injury to healthy tissue along the passage to the target vessel. Furthermore, once placed, the continuous stresses from blood flow and cardiac muscle activity created significant risks of thrombosis and damage to the vessel walls adjacent to the lesion, leading to restenosis. A major disadvantage of these types of stents were that their radial expansion was associated with significant shortening in their length, resulting in unpredictable longitudinal coverage when fully deployed.

Among subsequent designs, some of the most popular have been the Palmaz-Schatz slotted tube stents. Originally, the Palmaz-Schatz stents consisted of slotted stainless steel tubes comprising separate segments connected with articulations. Later designs incorporated spiral articulation for improved flexibility. These stents are delivered to the affected area by means of a balloon catheter, and are then expanded to the proper size. The Palmaz-Schatz designs exhibit moderate longitudinal shortening upon expansion, with some decrease in diameter, or recoil, after deployment. Furthermore, the expanded metal mesh is associated with relatively jagged terminal prongs, which increase the risk of thrombosis and/or restenosis.

Another type of stent involves a tube formed of a single strand of tantalum wire, wound in a sinusoidal helix; these are known as the Wiktor stents. They exhibit increased flexibility compared to the Palmaz-Schatz stents; however, they do not provide sufficient scaffolding support for many applications, including calcified or bulky vascular lesions. Further, the Wiktor stents also exhibit some recoil after radial expansion.

Another form of metal stent is a heat expandable device using Nitinol or a tin-coated, heat expandable coil. This type of stent is delivered to the affected area on a catheter capable of receiving heated fluids. Once properly situated, heated saline is passed through the portion of the catheter on which the stent is located, causing the stent to expand. Numerous difficulties have been encountered with this device, including difficulty in obtaining reliable expansion, and difficulties in maintaining the stent in its expanded state.

Self-expanding stents are problematic in that exact sizing, within 0.1 to 0.2 mm expanded diameter, is necessary to adequately reduce restenosis. However, self-expanding stents are currently available only in 0.5 mm increments. Thus, greater flexibility in expanded size is needed.

Stents can be deployed in a body lumen by means appropriate to their design. One such method would be to fit the collapsed stent over an inflatable element of a balloon catheter and expand the balloon to force the stent into contact with the body lumen. As the balloon is inflated, the problem material in the vessel is compressed in a direction generally perpendicular to the wall of the vessel which, consequently, dilates the vessel to facilitate blood flow therethrough. Radial expansion of the coronary artery occurs in several different dimensions and is related to the nature of the plaque. Soft, fatty plaque deposits are flattened by the balloon and hardened deposits are cracked and split to enlarge the lumen. It is desirable to have the stent radially expand in a uniform manner.

Alternatively, the stent may be mounted onto a catheter that holds the stent as it is delivered through the body lumen and then releases the stent and allows it to self-expand into contact with the body lumen. This deployment is effected after the stent has been introduced percutaneously, transported transluminally and positioned at a desired location by means of the catheter.

In summary, significant difficulties have been encountered with all prior art stents. Each has its percentage of thrombosis, restenosis and tissue in-growth, as well as various design-specific disadvantages. Thus, there is a need for an improved stent: one that has relatively smooth marginal edges, to minimize restenosis; one that is small enough and flexible enough when collapsed to permit delivery to the affected area; one that is sufficiently flexible upon deployment to conform to the shape of the affected body lumen; one that expands uniformly to a desired diameter, without change in length; one that maintains the expanded size, without significant recoil; and one that has sufficient scaffolding to provide a clear through-lumen.

SUMMARY OF THE INVENTION

The present invention is a radially expandable support device, or stent, for use in an artery or any other body lumen. The expandable intraluminal stent comprises a tubular member formed from at least one series of overlapping ladder elements. Each ladder element has two elongated ribs and two end rungs affixed to the elongated ribs. The elongated ribs are slidably engaged by a portion of the end rungs of adjacent ladder elements, such that sliding of the elongated ribs creates a variable distance between the end rungs of adjacent ladder elements. The tubular member has a first diameter in which the distance between end rungs of adjacent ladder elements is collapsed, and a second diameter, in which the distance between end rungs of adjacent ladder elements is expanded.

The elongated ribs may have a plurality of slots adapted to engage a lockout tab on the end rung of an adjacent ladder element. The slotted-ribs and lockout tabs permit the end rungs to slide apart, thereby expanding the diameter of the tubular member. However, the lockout tabs engage the slots to prevent the end rungs from sliding back toward a more collapsed state.

The expandable stent may expand from the first collapsed diameter to the second, expanded diameter upon application from inside the tubular member of a radially outwardly extending force. Alternatively, the tubular member may self-expand to the second, expanded diameter upon removal of a restraint, which holds the tubular member in the first, collapsed diameter.

The expandable stent in accordance with one embodiment of the present invention may be made from an alloy selected from the group consisting of stainless steel, elgiloy, tantalum, titanium and Nitinol. In a variation, the stent may be made from at least one biodegradable material selected from the group consisting of polypeptides, polydepsipeptides, nylon copolymides, aliphatic polyesters, polydihydropyrans, polyphosphazenes, polyorthoesters, polycyanoacrylates, and their derivatives. Bioactive agents may also be incorporated into the biodegradable material. These agents may be selected from the group consisting of heparin, hirudin, warfarin, ticlopidine, dipyridamole, GPIIb/IIIa receptor blockers, thromboxane inhibitors, serotonin antagonists, prostanoids, calcium channel blockers, PDGF antagonists, ACE inhibitors, angiopeptin, enoxapalin, colchicine, steroids, non-steroidal anti-inflammatory drugs, VEGF, adenovirus, enzymes, sterol, hydroxylase, antisense sequences, fish oils, HMG, Co-A reductase inhibitors, ibutilide fumarate, adenylcyclase, growth factors, nitric oxide, proteins, peptides and carbohydrates.

The stent of the present invention may be ultra-thin. Accordingly, it may have an expanded thickness in a range from about 0.01 to about 0.0001 inches. More preferably, the thickness of the expanded stent is less than about 0.0007 inches.

The maximum circumference (and diameter) of the expandable stent is defined by the number of ladder elements which comprise a series, whereas the axial length of the stent is defined by the number of series employed. The stent may also comprise longitudinal support elements, which couple the end rungs from adjacent series of ladder elements, thereby fixing the coupled series of ladder elements at a constant longitudinal distance from one another. The longitudinal support elements and end rungs may be oriented either substantially parallel to the longitudinal axis of the stent or diagonally, at an angle to the longitudinal axis. In one embodiment, a longitudinal backbone runs the entire axial length of the stent.

BRIEF DESCRIPTION OF THE DRAWINGS

FIG. 17 is an enlarged detail view showing another embodiment of a one-way locking means.

FIG. 18 is an enlarged detail view showing another embodiment of a two-way locking means.

FIG. 19 is an enlarged detail view showing another embodiment of a two-way locking means.

FIG. 20 is an enlarged detail view showing another embodiment of a one-way locking means.

FIG. 21 is an enlarged detail view showing another embodiment of a one-way locking means.

FIG. 22 is an enlarged detail view showing another embodiment of the locking means.

DETAILED DESCRIPTION OF THE PREFERRED EMBODIMENT

Figure 1:
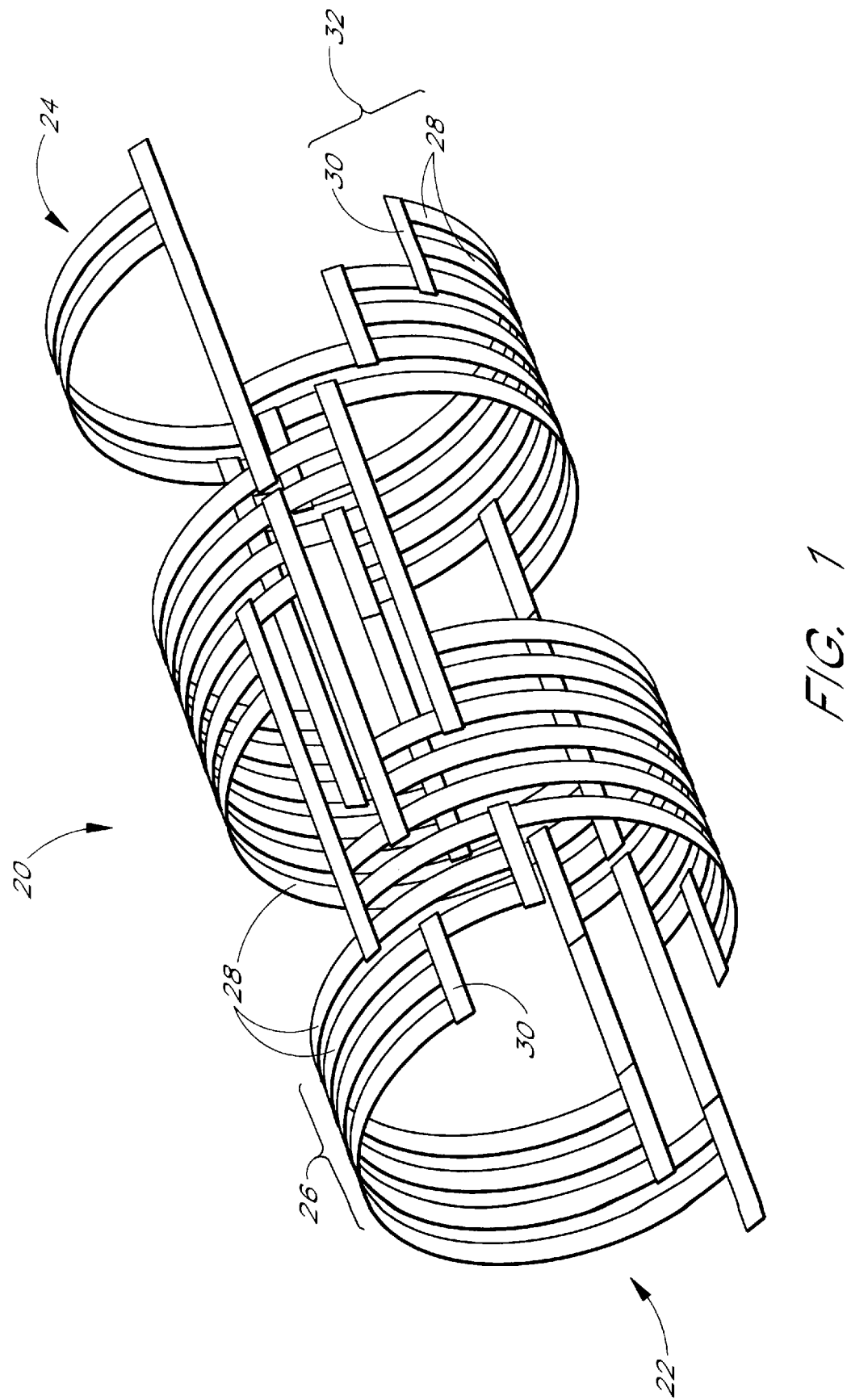
FIG. 1 is a perspective view of an embodiment of the expandable stent in accordance with the present invention

Referring to FIG. 1, there is shown a perspective view of an embodiment of the expandable stent in accordance with the present invention. The tubular member 20 has a proximal end 22 and a distal end 24. The tubular member 20 has ribbed walls 26 comprising elongated ribs 28, oriented circumferentially, and end rungs 30, oriented in the longitudinal axis. Elongated ribs 28 are substantially parallel to one another and perpendicular to the longitudinal axis of the tubular member. The ribs are attached to end rungs 30 to form rectangular ladder elements 32, which are the basic unit of construction.

Figure 2B:
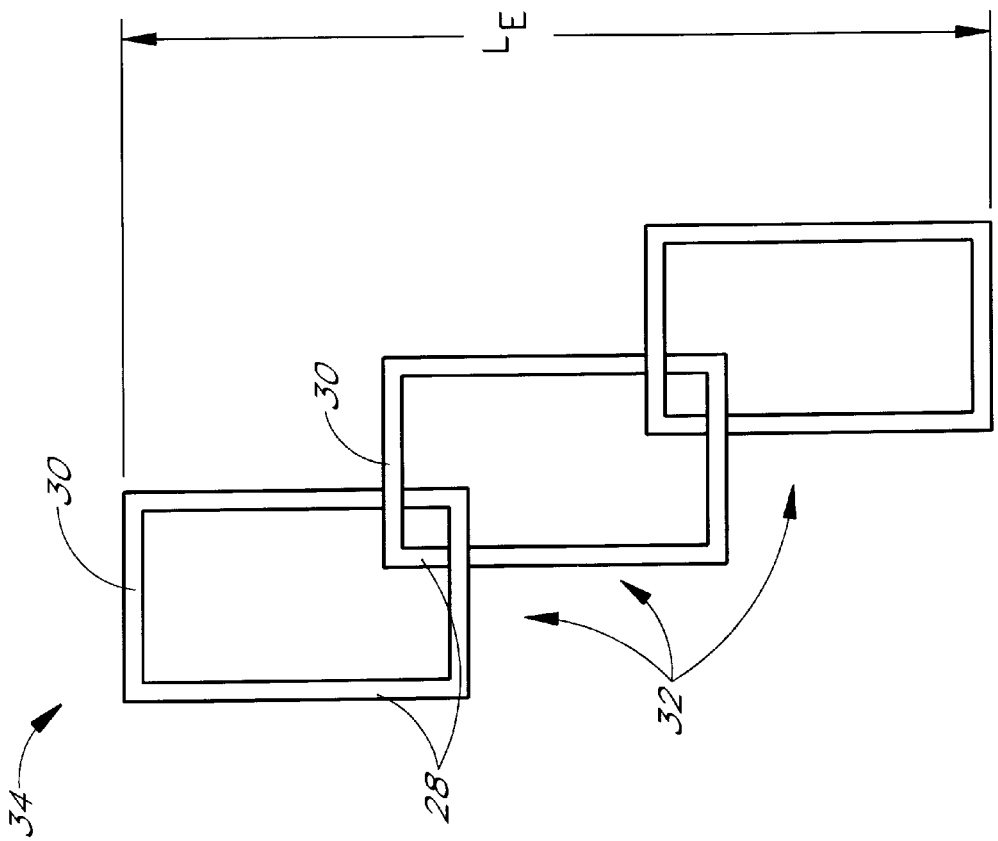
FIG. 2 is a plan view of an expandable stent in accordance with the present invention, illustrating a series of overlapping ladder elements.
Figure 2A:
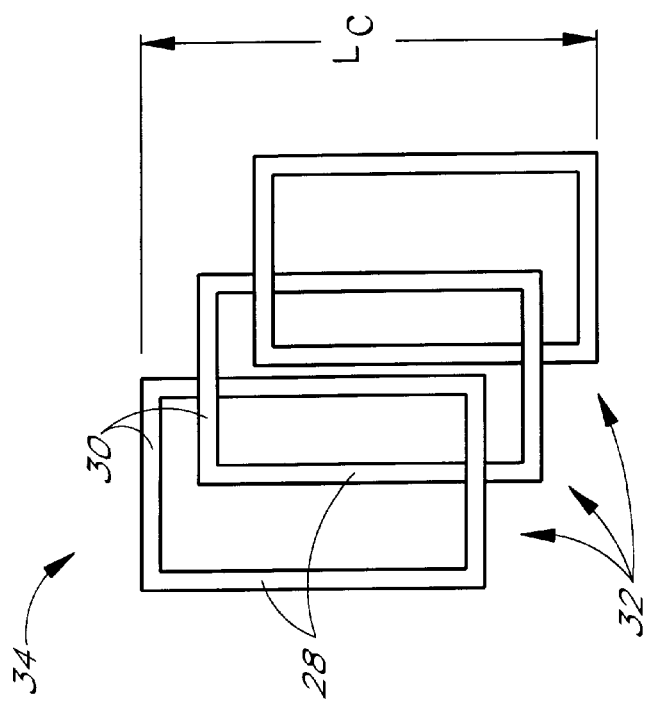

Referring to FIG. 2, a plan view of a stent in accordance with the present invention shows a series 34 of overlapping ladder elements 32. The elongated ribs 28 from one ladder element are slidably engaged by the end rungs 30 of adjacent ladder elements, such that the ladder elements can slide together, as shown in FIG. 2A, yielding a collapsed length ($L_C$), or the ladder elements can slide apart, as shown in FIG. 2B, yielding an expanded length ($L_E$). The number of ladder elements which comprise a series 34 can vary within the range of about 2 to 12, preferably between 3 to 8 ladder elements per series. Thus, the stent can be manufactured having a variety of expansion ratios.

As the number of overlapping ladder elements increases, the maximum $L_E$ also increases as does the expansion ratio ($L_E$:$L_C$). The circumference of the tubular member is defined when the series 34 is rolled to form a tubular member. It is important to note that the expanded length ($L_E$), and consequently, the expanded diameter and circumference of any given stent made in accordance with the present invention, may vary depending on the amount of sliding which is induced during deployment. Thus, the tubular member of the stent may have a first, collapsed diameter (defined by a collapsed distance between adjacent end rungs), and a second, expanded diameter (defined by an increased distance between adjacent end rungs), wherein the second diameter is variable and determined by the desired expanded internal diameter of the body passageway.

Figure 3:
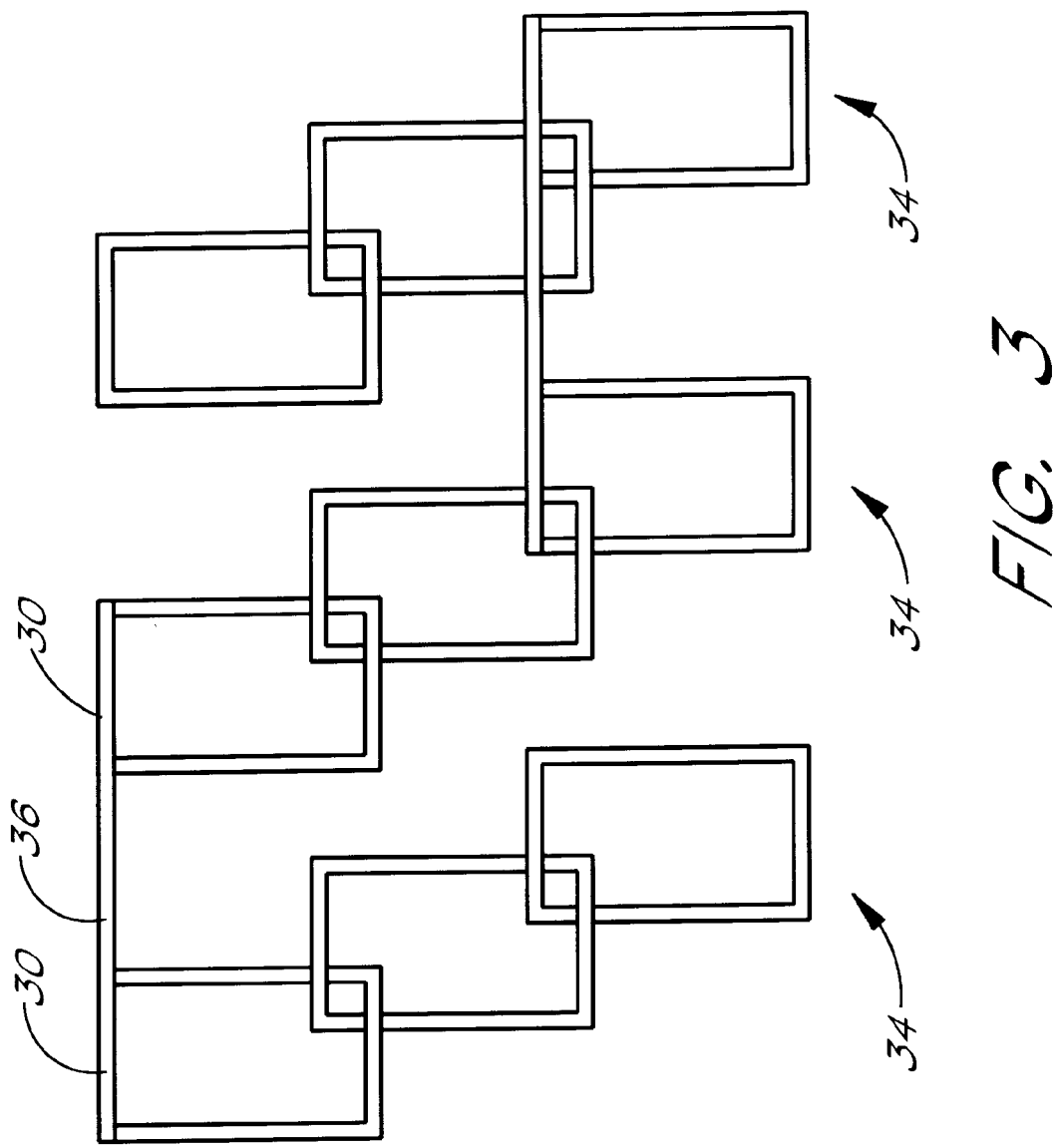
FIG. 3 is a plan view of an expandable stent in accordance with the present invention, showing three series of three ladder elements each.

Whereas the number of ladder elements per series defines the maximum circumference of the tubular member, and thereby the diameter of the tubular member, the total axial length of the tubular member is determined by the number of series which are joined longitudinally to form the stent Referring to FIG. 3, a plan view of a stent in accordance with the present invention illustrates three series of three ladder elements each. Each series is coupled with the adjacent series by a longitudinal support element 36, which is attached to the end rungs 30 from adjacent series. The longitudinal support elements 36, not only serve as coupling means for joining one series to the next, they also fix the longitudinal distance between adjacent series and provide axial strength, which prevents shortening or lengthening of the expanding stent during deployment.

Figure 4:
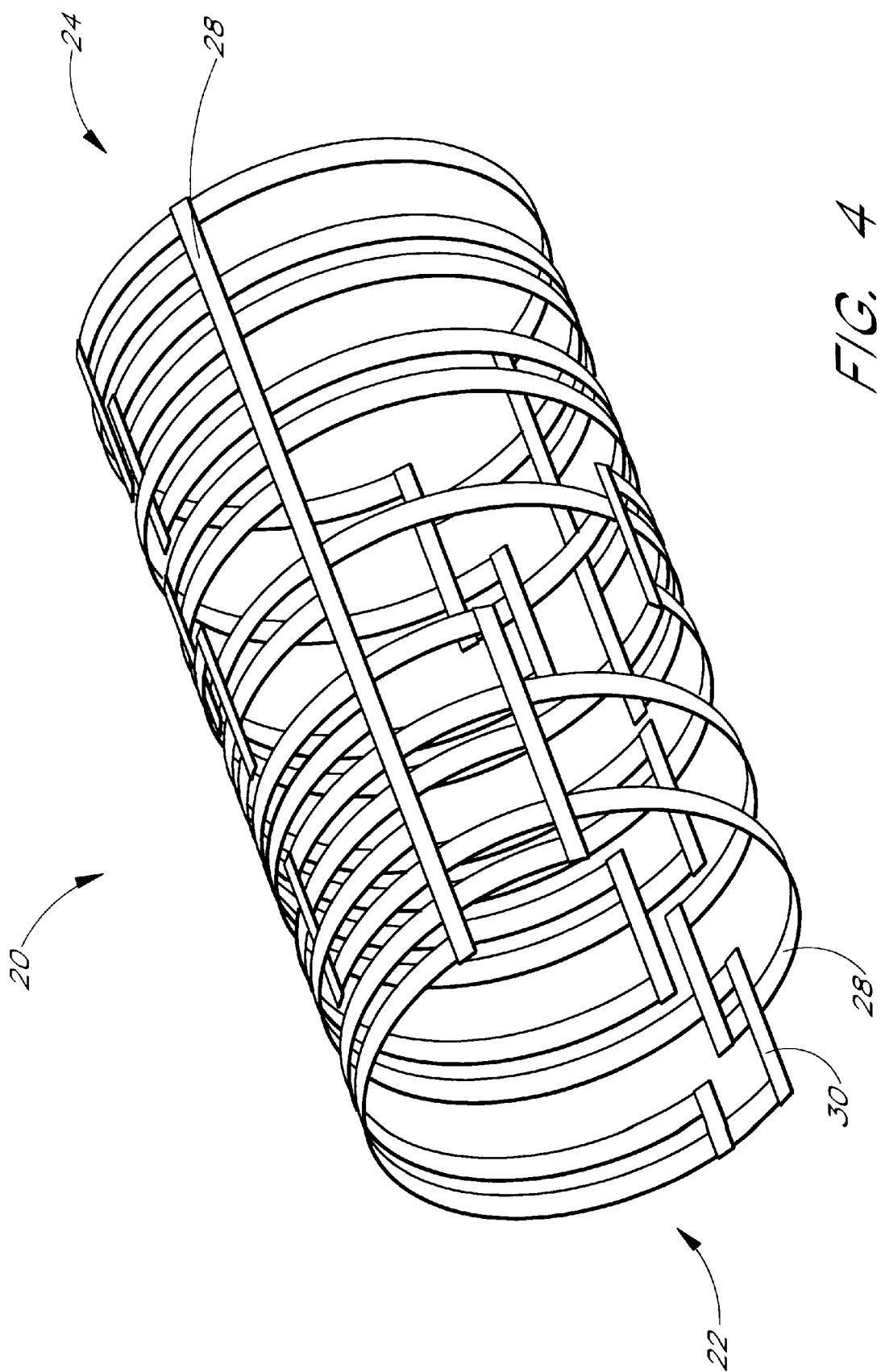
FIG. 4 is a perspective view of an embodiment of the present invention showing a longitudinal backbone spanning the entire length of the tubular member.
Figure 5:
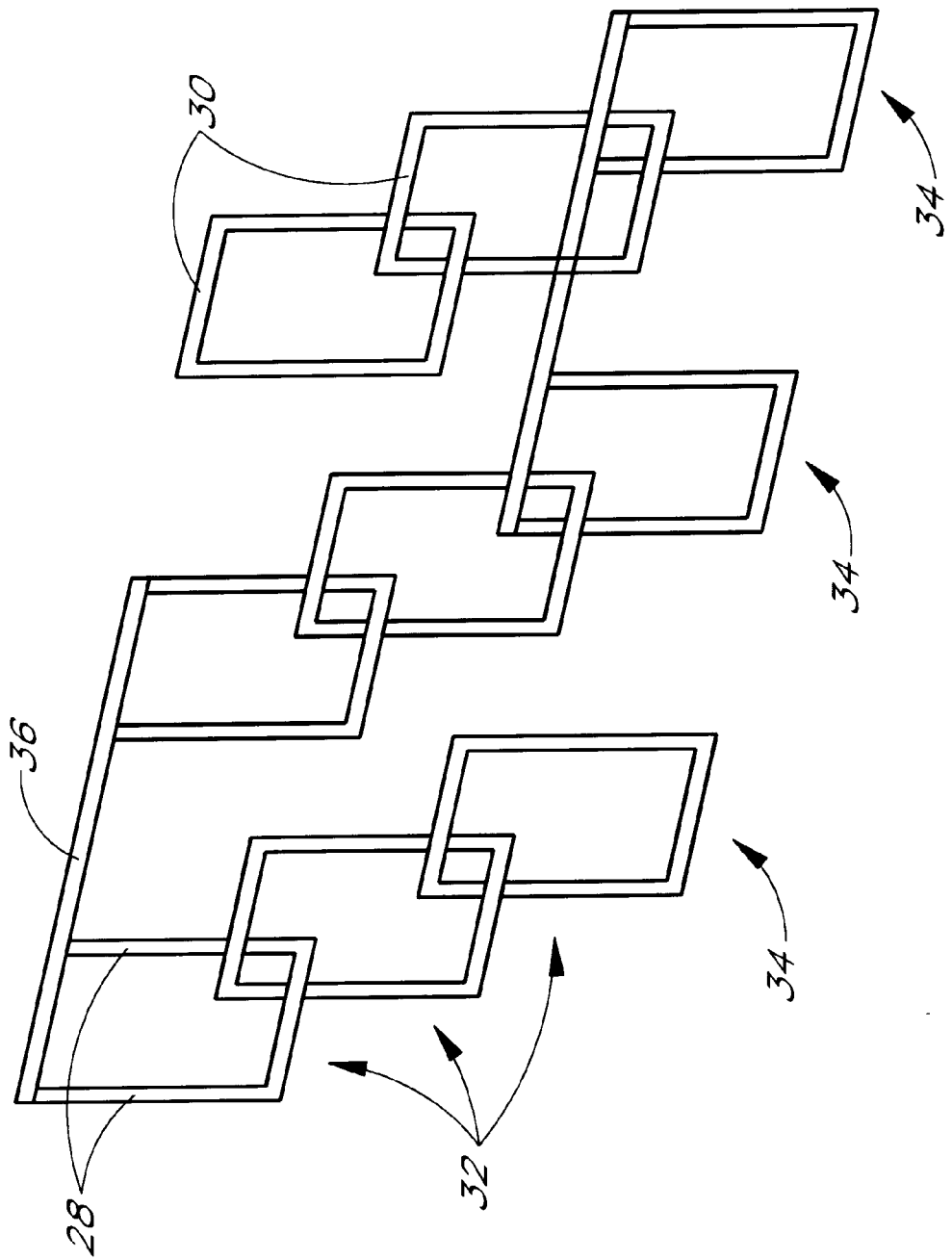
FIG. 5 is a plan view of another preferred embodiment of the present invention having diagonal end rungs and longitudinal Support elements.
Figure 6:
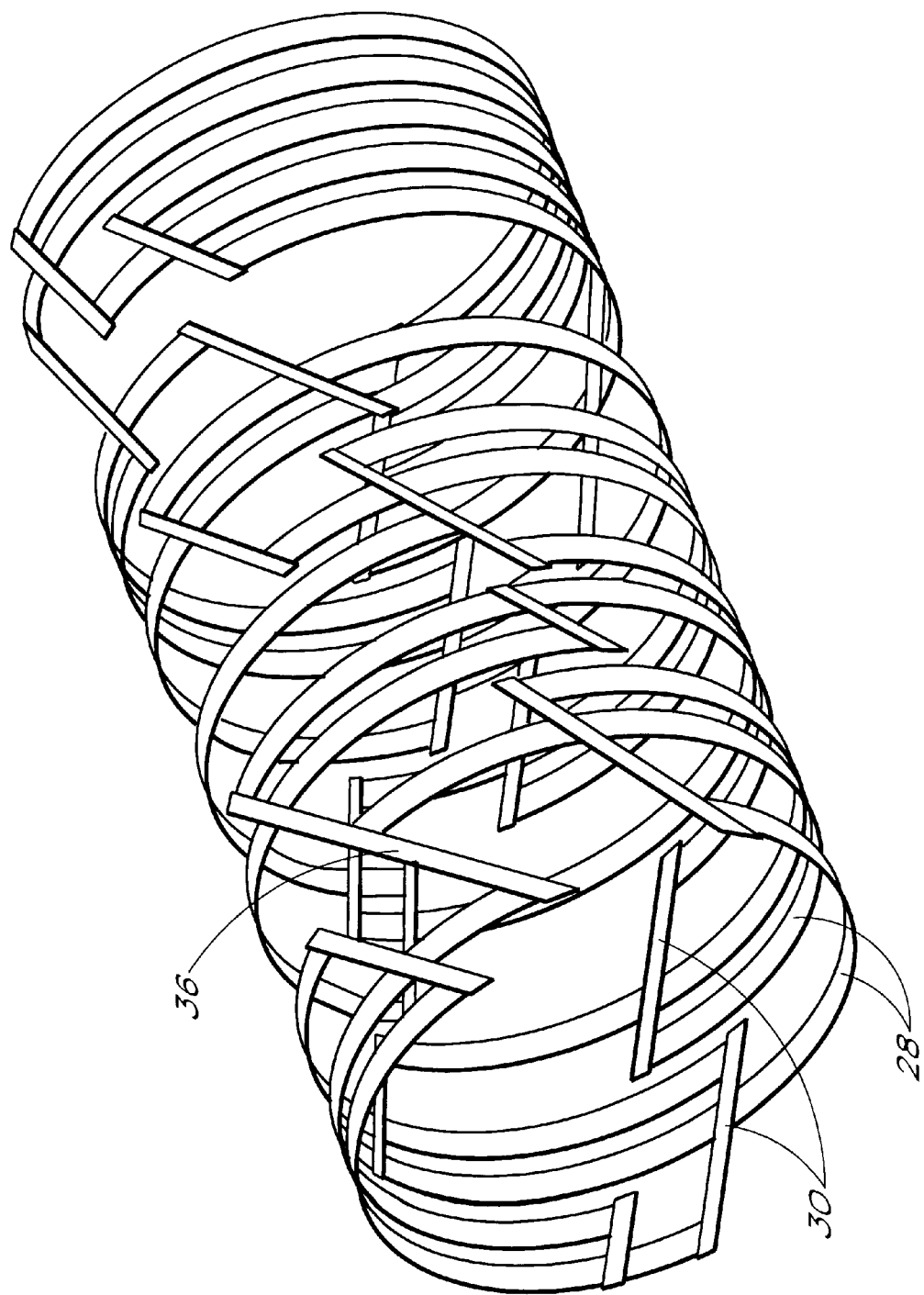
FIG. 6 is a perspective view of the embodiment illustrated in FIG. 5.

Referring to FIG. 4, there is illustrated a perspective view of an embodiment of the present invention showing a tubular member 20 having a proximal 22 and distal 24 end. The elongated ribs 28 are bowed to form a circumferential arc. The ribs are attached to end rungs 30. In this embodiment, a longitudinal backbone 38, spanning the entire length of the tubular member connects all of the end rungs that lie along a straight line in the longitudinal axis. The backbone functions just like the individual longitudinal support elements 36, by coupling adjacent series to one another, and providing axial strength. However, while employment of backbone provides optimal axial strength, preventing changes in length during deployment, an embodiment of the stent having a backbone also reduces the flexibility of the prosthesis in conforming to bends in the target vessel. Thus, while stents may incorporate a longitudinal backbone in accordance with the present invention for use in straight segments of target vessels, it is important to recognize that the backbones are an optional feature, and that flexible stents in accordance with the present invention, having only the shorter longitudinal support elements (illustrated in FIG. 3) or diagonally disposed end rungs and longitudinal support elements provide another preferred embodiment (see below; FIG. 5 and 6).

Referring to FIG. 5, there is shown a plan view of another preferred embodiment of the present invention. The tubular member is again constructed from separate series 34 of ladder elements 32, each comprising elongated ribs 28 and end rungs 30, the rungs from one series being connected to end rungs on the adjacent series by longitudinal support elements 36. However, whereas the end rungs 30 and longitudinal support elements 36 run parallel to the longitudinal axis of the tubular member in FIG. 3, they may alternatively, run at an angle diagonal to the longitudinal axis of the tubular member, as illustrated in FIG. 5. Thus, the resulting ladder element assumes the shape of a parallelogram, instead of a rectangle. The angle at which the end rungs and longitudinal support elements deviate from the longitudinal axis may vary between 0 and 60 degrees. More preferably the angle will be in the range of about 15 and 60 degrees. Most preferably, the angle varies between 15 and 45 degrees.

A perspective view of this embodiment is illustrated in FIG. 6, having diagonal end rungs 30 and longitudinal support elements 36. The elongated ribs 28 in this embodiment are substantially parallel to one another and perpendicularly disposed to the longitudinal axis. The end rungs 30, however, do not run parallel to the longitudinal axis in this stent. Instead, the end rungs 30 are diagonally aligned at an angle to the longitudinal axis. Any longitudinal support elements employed in constructing a stent in accordance with this preferred embodiment of the present invention, are also diagonally aligned at the same angle to the longitudinal axis as the end rungs.

It is important to appreciate the many layers of design flexibility embodied by the present invention. First, referring back to FIGS. 2A and 2B, stent diameter may be varied readily during manufacture by varying the number of ladder elements 32 per series 34. The collapsed ($L_C$) and expanded ($L_E$) circumferential distance, and therefore tubular diameter, is defined by the distance between the first and last end rung in a series. Specifically, expandable stents in accordance with the present invention may range in diameter from about 0.5–5.0 mm in the collapsed state to about 1.0–200 mm in the expanded state. More preferably the diameters may range from about 0.7–1.8 mm collapsed to about 2.0–8.0 mm expanded.

Next, referring back to FIGS. 3 and 4, the total axial length of the stent may be varied by employing different numbers of series 34, connected to one another in the longitudinal axis by longitudinal support elements 36 and/or longitudinal backbones. Differences in the axial length of the end rungs 30 will also vary the total axial length of the stent. Generally, for traditional stent applications, at least two series will be employed; however, it is conceived that collar stents in accordance with the present invention, comprising a single series of ladder elements, may be used to secure a polymeric sleeve or graft against a vessel wall at proximal and distal ends flanking an aneurysm. Specifically, stents in accordance with the present invention may range in total length from about 1.0–200 mm. More preferably, the lengths may range from about 4.0–40 mm, and most preferably, from about 16–24 mm.

Another parameter of design flexibility involves delivery and implanted flexibility. Delivery flexibility allows curving of the stent on the catheter to facilitate delivery to the target site. Implant flexibility allows for curving of the stent to conform to curved vessels and lumen. As stent flexibility is increased, axial strength and rigidity are compromised. The manufacturer of stents in accordance with the present invention has numerous options for selecting the proper combination of flexibility and axial strength for a given clinical application. One option for varying flexibility involves adjusting the number of longitudinal support elements 36. For instance, if a series 34 of ladder elements 32 is not connected to its adjacent series at all, the resulting segmented stent will afford maximal flexibility. On the other hand, if longitudinal support elements 36 connect each complementary end rung 30 in adjacent series, very little flexibility is fostered. But, the first, more flexible embodiment, will be more susceptible to axial compression, while the second, less flexible embodiment will exhibit much enhanced axial strength. As discussed above, the inclusion of a longitudinal backbone 38 would greatly increase axial strength and concomitantly, reduce delivery and implantation flexibility. The full range of engineered flexibility and axial strength are encompassed within the spirit of the present invention.

As discussed above, referring to FIGS. 5 and 6, another option through which the manufacturer may vary the flexibility/axial strength ratio would be to employ end rungs 30 and longitudinal support elements 36 which run diagonal to the longitudinal axis of the tubular member. Indeed, stent flexibility can be varied by incorporating different numbers of diagonal longitudinal support elements 36 and by varying the angle of deflection. The smaller the angle of deflection from the longitudinal axis, the less flexibility (and the greater the axial strength). Thus, stent designs in accordance with the present invention may be optimized for particular clinical applications.

Figure 7:
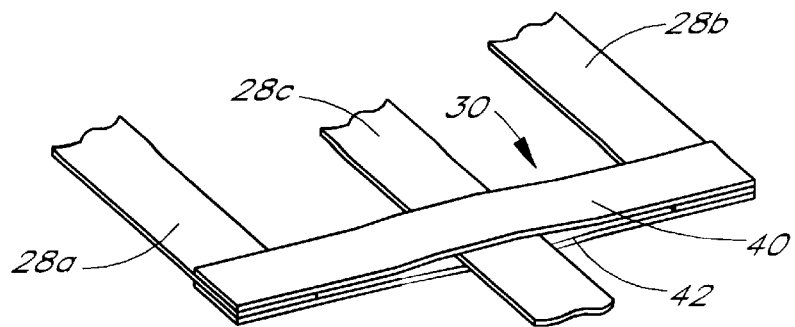
FIG. 7 is an enlarged detail view of a portion of an elongated rib slidably engaged by the end rung of an adjacent ladder element.

Referring to FIG. 7, there is shown a detail view of one embodiment of an elongated rib 28c slidably engaged in an end rung 30. The end rung 30 is formed from two preferably identical rung leaves, 40 and 42, which are fastened to the elongated ribs 28a and 28b from the same ladder element, in a sandwich-like manner, thereby creating an open passage through which the elongated rib 28c from an adjacent ladder element may slide. Many embodiments for the slidable engagement means are envisioned. Paired parallel slots formed in the end rung may be used to engage the elongated ribs, wherein the ribs pass through one slot and return through the other in a weave-like fashion. Alternatively, the end rung material between the paired slots may be displaced vertically from the surface of the end rung during manufacture, thereby creating a passage through which a rib may slide without bending upward and downward relative to the surface of the end rung. Similarly, a separate strap or wire guide may be affixed on the end rung to create a channel through which the engaged rib may slide. Any other slidable articulations known in the art are also conceived as potential engagement means.

Figure 8:
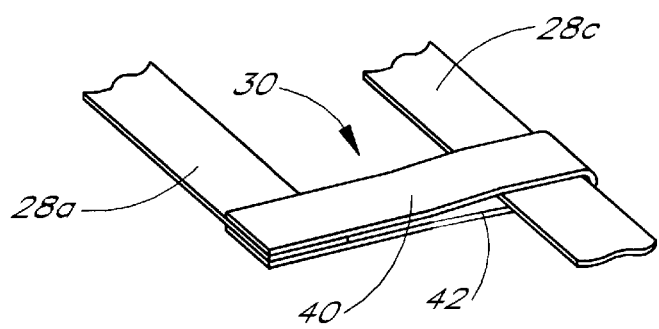
FIG. 8 is an enlarged detail view of a portion of an elongated rib slidably engaged by the end rung of an adjacent ladder element.

In addition to the variety of configurations for the slidable engagement means, the locations of these slidable engagement means on the ladder elements may also vary. For example, FIG. 8, shows an elongated rib 28c slidably engaged in an end rung 30, however, instead of the engagement means being located between ribs in one ladder element (as illustrated in FIG. 7), the engagement means shown in FIG. 8 is located at a free end of an end rung 30. The slidably engaged elongated rib 28c passes through a passage created by folding the end rung 30 about the fixed rib 28a. The resultant upper 40 and lower 42 leaves of the end rung 30 define the passage. Thus, it is envisioned that different embodiments of the stent according to the present invention, will employ engagement means located either at the junctions between ribs and end rungs on a given ladder element, between ribs (as shown in FIG. 7), at terminal end rungs which are only attached to one rib (as shown in FIG. 8), or at terminal end rungs which are attached to two or more ribs, but which extend beyond that axial distance of the ladder element defined between its ribs.

Figure 9:
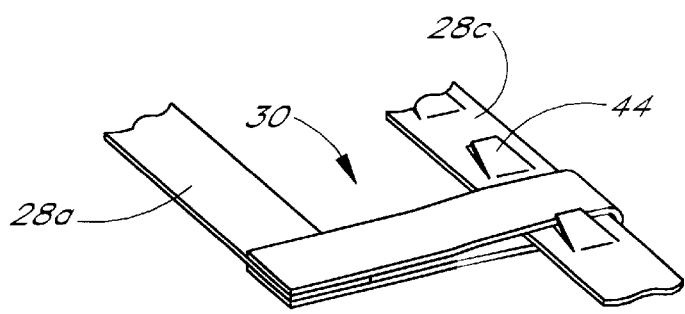
FIG. 9 is an enlarged detail view showing an embodiment of a one-way locking means.

Referring to FIGS. 9–29, there are illustrated many different embodiments of locking means. For clarity, all of the locking means have been illustrated on the least cluttered locations for engagement means, the terminal end rungs 30 attached to a single fixed rib 28a. However, it is important to note that these locking means may be incorporated within slidable engagement means at any of the above discussed locations. FIG. 9 shows one embodiment of the locking means having stops 44 on the slidably engaged rib 28c. The stops 44 can pass through the engagement means in only one direction (expanding the stent). In this embodiment, the stops 44 are in the form or tabs that protrude at an angle upward off the surface of the rib 28c. These tab stops 44 are depressed when passing through the engagement means and then spring out, thereby preventing the slidably engaged rib 28c from moving relative to the end rung 30, back toward a more collapsed configuration.

Figure 10:
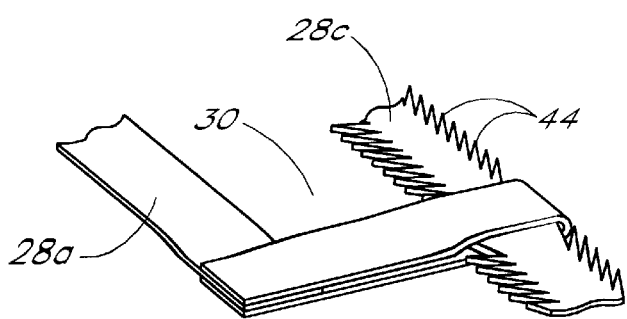
FIG. 10 is an enlarged detail view showing another embodiment of a one-way locking means.

Referring to FIG. 10, another embodiment of the locking means is shown, wherein the slidably engaged rib 28c is notched on its edges in such a manner as to permit movement in only one direction relative to the end rung 30. In this embodiment, the notched edges of the engaged rib 28c form the stops 44. Again, the stops are depressed as they pass through the engagement means and spring out laterally to prevent recoil.

Figure 11:
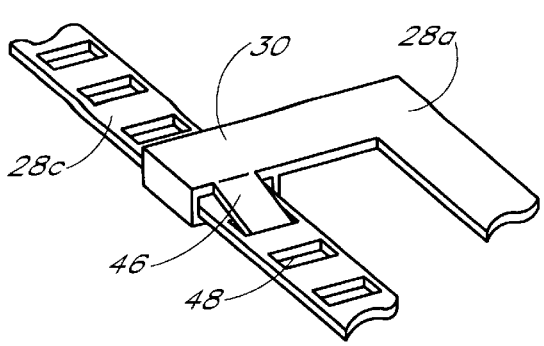
FIG. 11 is an enlarged detail view showing a preferred embodiment of a one-way locking means.
Figure 12:
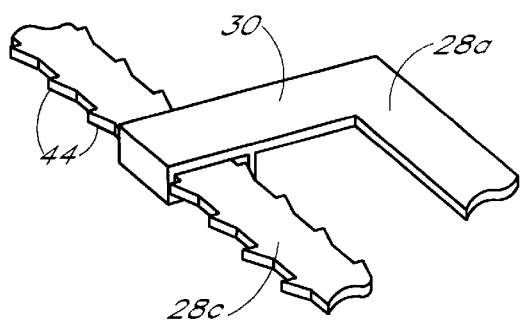
FIG. 12 is an enlarged detail view showing another embodiment of a one-way locking means.

Referring to FIG. 11, there is illustrated a preferred locking means in which a sprung tab 46 is attached to the engagement means and the slidably engaged rib 28c is modified to have a plurality of holes or notches 48 adapted to engage the sprung tab 46. The angle at which the tab 46 engages the holes 48 permits only one-way sliding. Referring to FIG. 12, there is shown another variation of the locking means illustrated in FIG. 10. Notched stops 44 in the slidably engaged rib 28c permit only one-way sliding.

Figure 13:
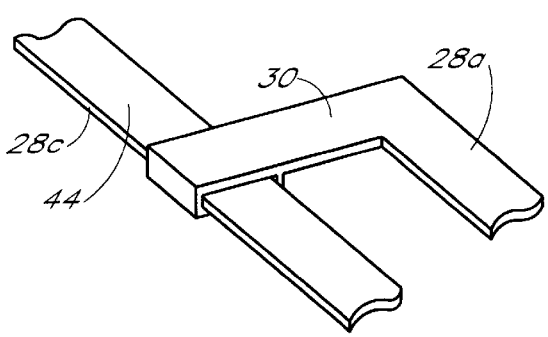
FIG. 13 is an enlarged detail view showing an embodiment of a two-way locking means.
Figure 14:
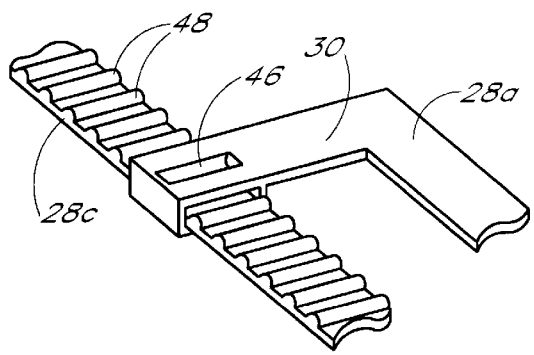
FIG. 14 is an enlarged detail view showing another embodiment of a two-way locking means.
Figure 15:
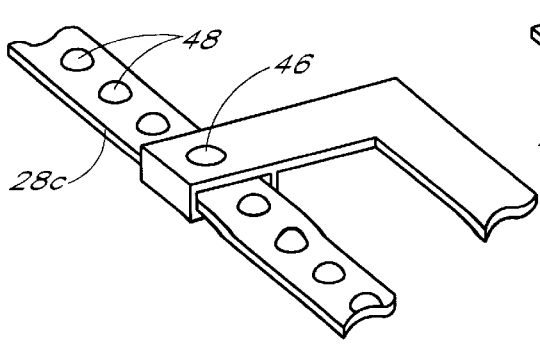
FIG. 15 is an enlarged detail view showing another embodiment of a two-way locking means.
Figure 16:
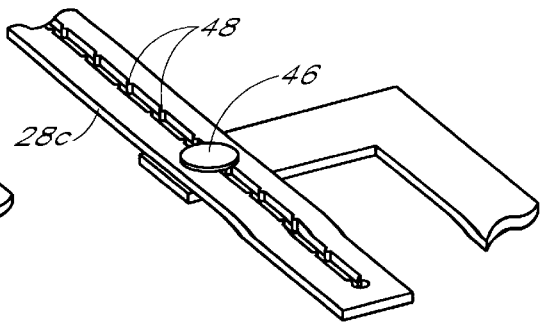
FIG. 16 is an enlarged detail view showing another embodiment of a two-way locking means.

Referring to FIGS. 13–16, there are shown a variety of locking means that operate by resisting sliding in either direction. Effectiveness of these embodiments is based on deployment using high pressure balloon catheters. Thus, the collapsed stent is deployed by inflating the balloon, which exerts sufficient radial pressure to overcome the resisting force of the locking means. For example, FIG. 13 shows a friction-based locking means. The stop 44 is created by a rough surface on the sliding rib 28c. Once forcibly deployed using the balloon catheter, the resistance to sliding due to friction would be sufficient to prevent recoil, absent application of a radially inward force greater than or equal to the radially outward force exerted by the balloon during expansion. FIGS. 14–16 illustrate other embodiments of locking means that will resist sliding in either direction. The locking means shown in FIGS. 14 and 15 have a plurality of raised convex male stops 48 on the surface of the sliding rib 28c and a complementary concave female catch 46. As the rib 28c slides, the male stops 48 are engaged by the female catch 46, thereby resisting further sliding. Referring to FIG. 16 there is shown another variation, having a knob catch 46 attached to the end rung. The sliding rib 28c is modified to have a central channel, through which the knob catch passes. The channel has a repeating pattern of stops 48 cut into the channel, such that as the rib slides, the knob catch 46 lodges in the stops 48, thereby resisting further sliding.

Referring to FIG. 17, there is illustrated another variation in the notch 48 and stop 46 locking means, however, in this embodiment, the notches are cut laterally into a central channel in the sliding rib 28c, whereas the stop 46 is engineered to have depressible lateral catches which are adapted to permit one-way sliding of the rib 28c relative to the end rung.

FIGS. 18 and 19 illustrate additional embodiments of two-way locking means that resist sliding in either direction. The locking means shown in FIG. 18 have female dimples 48 in the lateral edges of the sliding rib 28c and male catches 46 within the engagement means. The male catches exhibit sufficient flexibility to flex outward during sliding, but then snapping into the dimples 48 as they enter the engagement means. The embodiment shown in FIG. 19 has female dimples 48 disposed laterally from a central channel and a male knob catch 46.

Another embodiment of a one-way locking means is shown in FIG. 20. The rib 28c has a central channel lined at regular intervals with angled stops 48 which are depressed as they pass through the engagement means 46, and then spring laterally outward to prevent recoil.

The locking means shown in FIG. 21 employs raised stops 48 on the sliding rib 28c. The stops 48 are angled to permit one-way sliding through a catch 46 housed in the engagement means. Likewise, the embodiment illustrated in FIG. 22 has raised stops 48, which are square-shaped and a sprung tab 46 having a complementary square-shaped hole adapted for receiving the raised stops 48. The sprung tab may be shaped to allow either one-way or two-way resistance.

Figure 23:
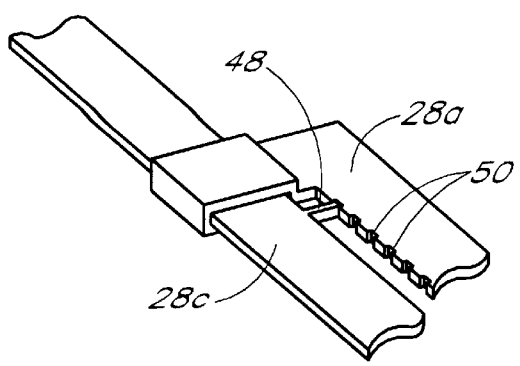
FIG. 23 is an enlarged detail view showing another embodiment of a two-way locking means.
Figure 24:
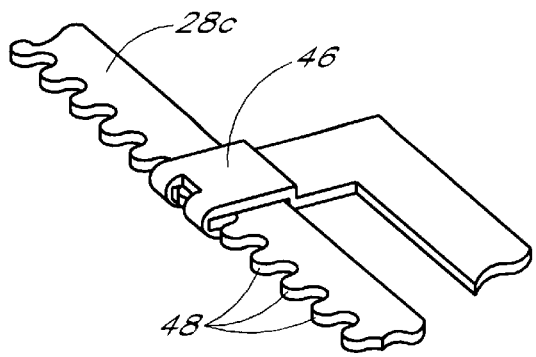
FIG. 24 is an enlarged detail view showing another embodiment of a two-way locking means.

The embodiment in FIG. 23 involves modification of both the sliding rib 28c as well as the fixed rib 28a. The sliding rib 28c has a deflectable tab stop 48, which interacts with regularly spaced dimpled catches on the lateral edge of the adjacent, fixed rib 28a FIG. 24 shows another two-way locking means, wherein the catch 46 on the engagement means interacts with notched stops 48 along the outer lateral edge of the sliding rib 28c.

Figure 25:
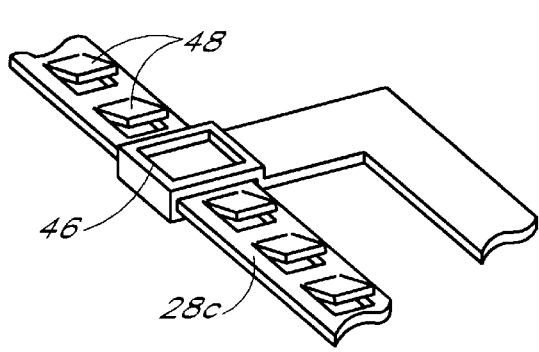
FIG. 25 is an enlarged detail view showing another embodiment of a one-way locking means.
Figure 26:
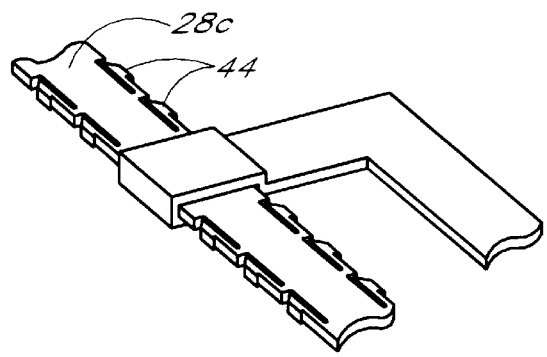
FIG. 26 is an enlarged detail view showing another embodiment of a one-way locking means.
Figure 27:
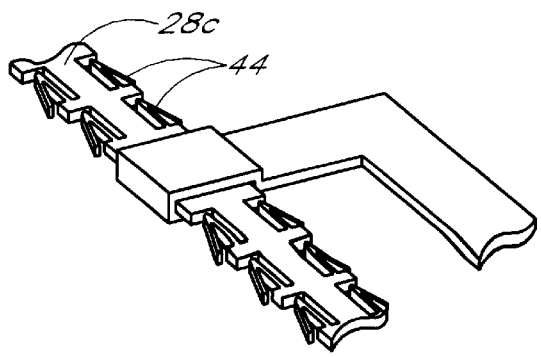
FIG. 27 is an enlarged detail view showing another embodiment of a one-way locking means.
Figure 28:
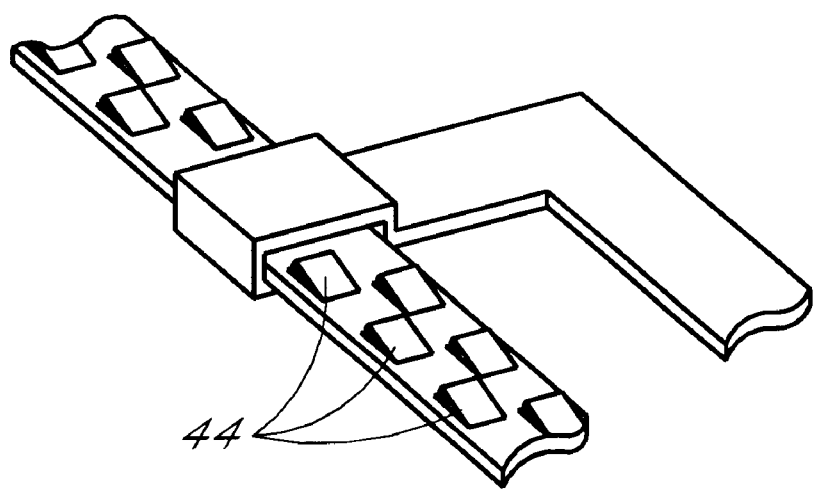
FIG. 28 is an enlarged detail view showing another preferred embodiment of a one-way locking means.
Figure 29:
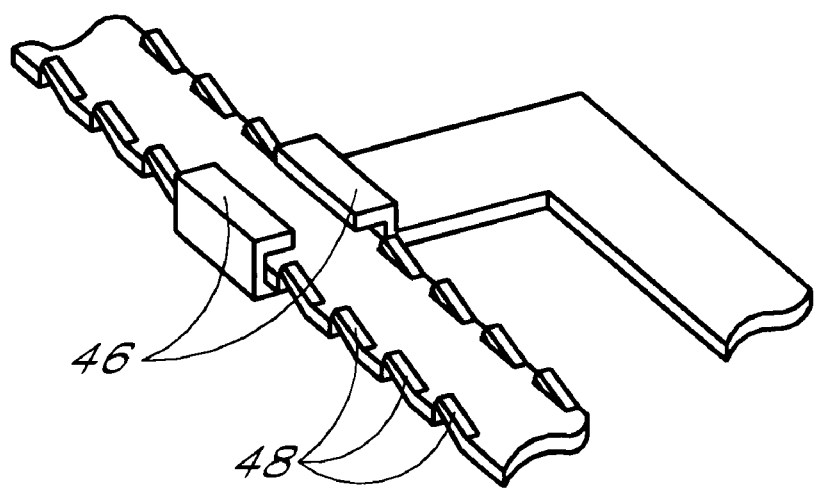
FIG. 29 is an enlarged detail view showing another preferred embodiment of a one-way locking means.

FIGS. 25–29 illustrate additional embodiments of one-way locking means. In FIGS. 25–27, the arresting mechanism involves the interaction of sprung tabs or stops 48 formed on the slidably engaged rib 28c and a catch or receiving means 46 formed by the engagement means on the end rung. FIGS. 28 and 29, are different in that the stops 48 are staggered on the surface of the sliding rib, in order to provide less recoil.

Typically, the elongated ribs, end rungs and longitudinal support elements would be made of the same material. Metals, such as stainless steel, elgiloy, tantalum, titanium, or a shape memory metal such as Nitinol, may be used. Plastic materials are also contemplated as useful variations. The stents embodied by the present invention may also be partially fabricated from or coated with a radiopaque metal such as gold, platinum, or tantalum to provide a fluoroscopic indication of the stent position within the lumen. Preferably, the proximal and distal ends would incorporate the radiopaque marker material. Alternatively, bismuth subcarbonate or any of the aforementioned radiopaque alloys could be loaded into an adhesive (e.g., Radiopaque Epoxy EP21BAS) and then placed on the stent at desirable locations.

It should be understood that all stent edges are preferably smooth and rounded to prevent thrombogenic processes and reduce the stimulation of intimal smooth muscle cell proliferation and potential restenosis. Furthermore, the stent material may be coated with materials that either reduce acute thrombosis, improve long-term blood vessel patency, or address non-vascular issues. Inert coating materials, such as parylene, may be utilized to provide a lubricious surface, prevent corrosion and reduce acute thrombosis. Further, bioactive agents may also be used to coat the stents. These include, but are not limited to: anticoagulants, such as heparin, hirudin, or warfarin; antiplatelet agents, such as ticlopidine, dipyridamole, or GPIIb/IIIa receptor blockers; thromboxane inhibitors; serotonin antagonists; prostanoids; calcium channel blockers; modulators of cell proliferation and migration (e.g. PDGF antagonists, ACE inhibitors, angiopeptin, enoxaparin, colchicine) and inflammation (steroids, non-steroidal anti-inflammatory drugs). Coating materials which may be used to improve long-term (longer than 48 hours) blood vessel patency include: angiogenic drugs such as, Vascular Endothelial Growth Factor (VEGF), adenovirus, enzymes, sterol, hydroxylase, and antisense technology; drugs which provide protection on consequences of ischemia; lipid lowering agents, such as fish oils, HMG, Co-A reductase inhibitors; others growth factors; nitric oxide; and proteins, peptides, carbohydrates. Finally, drugs that address non-vascular issues such as ibutilide fumarate (fibrillation/flutter), adenylcyclase (contractility), and others, may be applied as stent coatings.

In one embodiment, the expandable stent of the present invention is designed for intraluminal deployment by any of a variety of in situ expansion means, such as an inflatable balloon catheter in a conventional maimer or a polymeric plug that expands upon application of pressure. For example, the tubular body of the stent is first positioned to surround a portion of an inflatable balloon catheter. The stent, with the balloon catheter inside is configured at a first, collapsed diameter, wherein the circumferential distance between end rungs from adjacent ladder elements is collapsed. The stent and the inflatable balloon are percutaneously introduced into a body lumen, following a previously positioned guidewire in an over-the-wire angioplasty catheter system, and tracked by a fluoroscope, until the balloon portion and associated stent are positioned within the body passageway at the point where the stent is to be placed. Thereafter, the balloon is inflated and the stent is expanded by the balloon portion from the collapsed diameter to an expanded diameter. After the stent has been expanded to the desired final expanded diameter, the balloon is deflated and the catheter is withdrawn, leaving the stent in place.

The expanded diameter is variable and determined by the desired expanded internal diameter of the body passageway. Accordingly, the controlled expansion of the stent is not likely to cause a rupture of the body passageway. Furthermore, the stent will resist recoil because the locking means resist sliding of the elongated ribs within the engagement means on the end rungs. Thus, the expanded intraluminal stent will continue to exert radial pressure outward against the wall of the body passageway and will therefore, not migrate away from the desired location.

A self-expanding stent in accordance with another embodiment of the present invention may be deployed without the use of an external expansion force, e.g., a balloon. Instead, the stent may be maintained in its collapsed state on a catheter by a physical restraint, such as an outer sheath or other means. The catheter and stent are advanced as above to the target site, tracking the stent location by fluoroscopy (focusing on the radiopaque elements of the stent). Once at the target site, the stent collapsed around the underlying catheter may be deployed by removing the restraint. For instance, the restraining sheath may be withdrawn, thereby freeing the stent of the physical restraint. Alternatively, the sheath may remain stationary while the collapsed stent and catheter are pushed through the end of the sheath. Regardless of the means of removing the restraint, the stent is then permitted to expand naturally under the influence of its inherent spring force to its second, expanded diameter, bearing against the inner walls of the target passageway.

Figure 30:
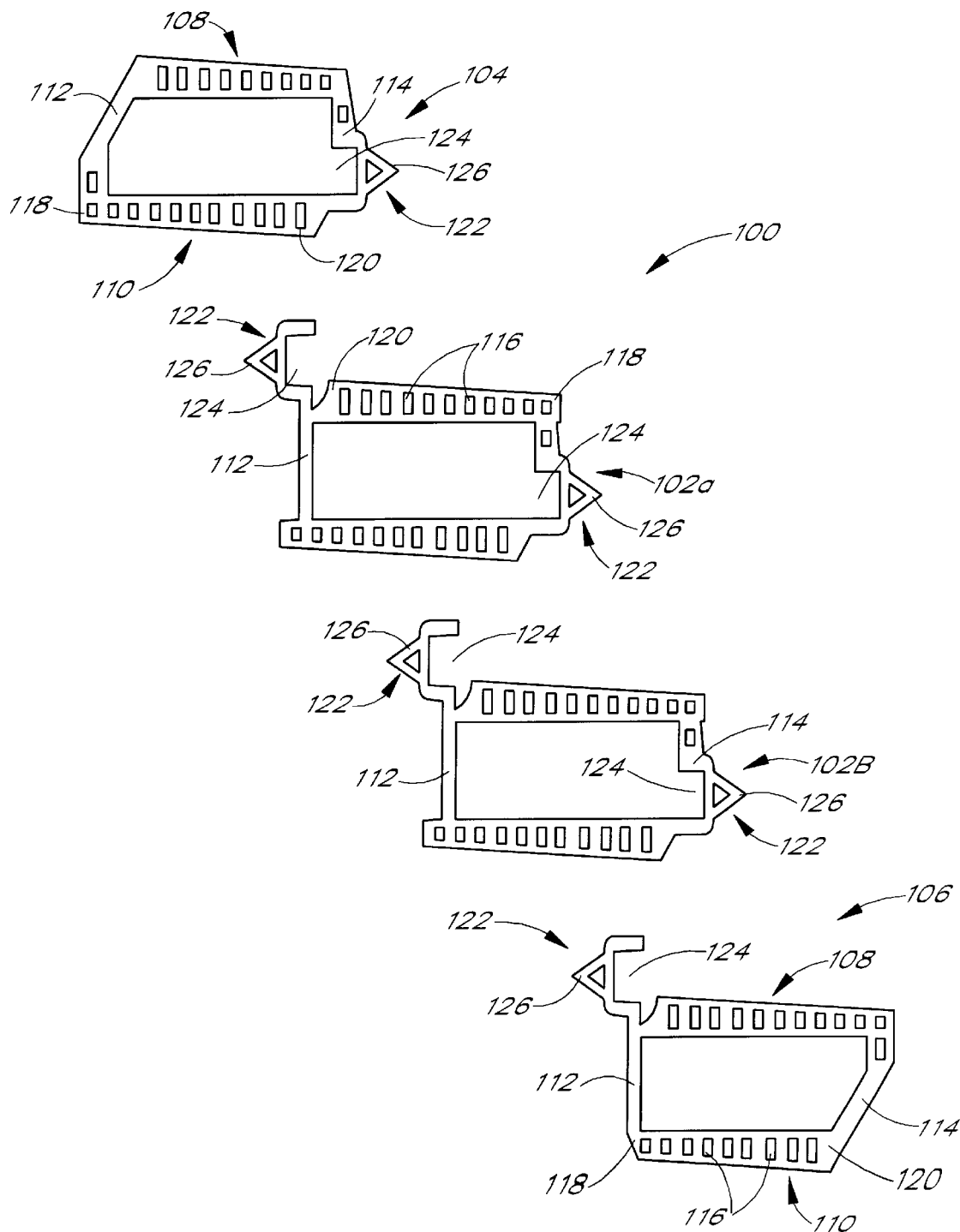
FIG. 30 is an exploded plan view of the variation of the expandable stent shown in FIG. 30, illustrating different middle and end ladder element designs and linkages.

With reference to FIG. 30, an exploded plan view of a low-profile variation of an expandable stent 100 in accordance with the present invention is shown, wherein the middle ladder elements 102a and 102b, and left and right end ladder elements, 104 and 106, have different configurations. Each ladder element comprises two elongated ribs, a top rib 108 and a bottom rib 110, and two end rungs, a left end rung 112 and a right end rung 114. The elongated ribs 108 and 110 have a plurality of slots 116. The ribs have a narrower end 118 and a wider end 120, wherein the slots 116 in the narrow end of the rib are narrower than the slots in the wider end and increase progressively in width as they go from the narrow end 118 to the wider end 120. Each ladder element has one or two lockout taps 122. The lockout tabs form a U-shaped region 124, which is adapted to slideably engage an elongated rib from an adjacent ladder element.

When the individual ladder elements are assembled, each top elongated rib 108 is designed to be in slideable contact above the bottom elongated rib 110 from the adjacent ladder element and to nest within the U-shaped region 124 formed by the lockout tab 122 in that adjacent ladder element .The wider end 120 of the top rib 108 abuts the narrower end 118 of the bottom rib 110. Thus, for example, when the top rib 108 of middle ladder element 102a lies above and adjacent to the bottom rib 110 in the left end ladder element 104, the top rib 108 of middle element 102a is nested within the U-shaped region 124 of the left end element 104. Once in this location, the lockout tab 122, which extends anteriorly from middle element 102a can be wrapped around the bottom rib 110 of the left end element 104 and tacked welded to the left end rung 112 of the middle element 102a. Each lockout tab 122 has a locking tip 126, which is angled to engage the slots of the rib that is slideably engaged in the U-shaped region 124 of the lockout tab 122. Consequently, the lockout tab 122 from the left end element 104 engages the slots in the top rib 108 of the middle ladder element 102a . Likewise, the lockout tab 122 of the middle element 102a engages the slots 116 in the bottom rib 110 of the left end ladder element 104, once the lockout tab has been folded posteriorly over the bottom rib 110, and fastened to the left end rung 112 of the middle ladder element 102a.

Figure 31A:
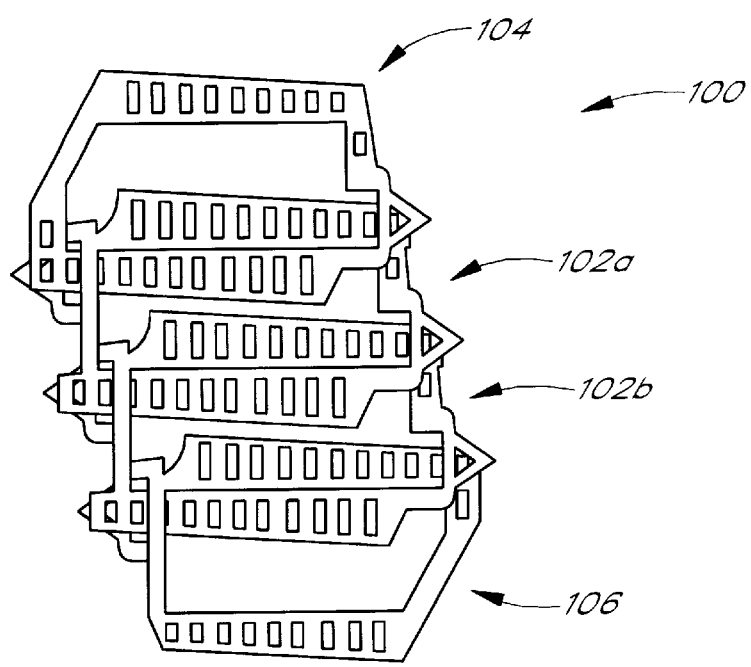
FIGS. 31A & B are plan views of a variation of the expandable stent in accordance with the present invention, illustrating a series of overlapping ladder elements in the expanded (A) and collapsed (B) state.

The other ladder elements are joined to one another in the same manner to form a series of the expandable stent of the present invention. A plan view of the assembled series is shown in FIG. 31A and B, illustrating the nested ladder elements, 104, 102a, 102b and 106, in the collapsed (A) and expanded (B) states.

The variation of the expandable stent described with reference to FIGS. 30 and 31 exhibits a low profile. The ladder elements of the stent may have a wall thickness in the range of about 0.01 to about 0.0001 inches. Preferably the thickness of the ladder element walls is less than about 0.0007 inches; 0.0014 inches at cross-over points. For example, when collapsed upon a delivery catheter, this variation does not have the individual ladder elements overlap. In combination with thinner material, the collapsed profile may be much lower than other stent designs. This feature is highly desirable to enable the stent to cross tight obstructions and may allow for direct treatment of diseased vessel without predilation of lesion with separate balloon catheter. This is in contrast to stents made of deformable materials which result in thicker stents, or sheet stents that coil around themselves in the collapsed state, producing several layers of stent material and giving high mounted profiles and very stiff collapsed and expanded states.

Figure 31B:
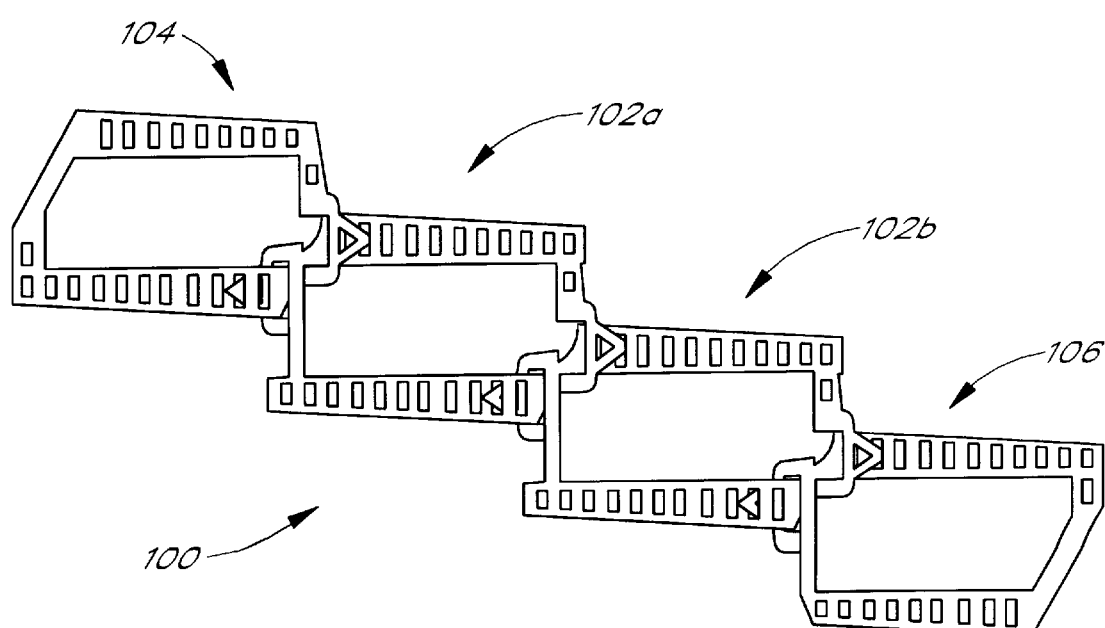

The lockout design in the low-profile embodiment of the expandable stent shown in FIGS. 30 and 31 employs lockout tabs 122 that can engage one of many slots 116, similar to a hose clamp. In order to reduce expansion friction, the lockout tabs in this variation are offset where ladder elements cross each other. Consequently, when assembled, there are at most two layers of materials with the third layer offset. This design results in lower expansion forces and collapsed profile. Potential "over-nesting", wherein a corner of a ladder element tucks under the U-shaped region 124 of the tab, is prevented by making sure that the dimensions of the ladder length, i.e., the elongated ribs 108 and 110, are sufficiently long. The extra length insures that the wide end 120 of the elongated rib 108 and 110 will be too large to fit under the U-shaped region 124. Alternatively, over-nesting can be prevented by including a stop to prevent over-contraction, as will be understood by those of skill in the art.

The elongated ribs 108 and 110 of the ladder elements in the low-profile variation of the expandable stent may vary in width along their length. For instance, in the collapsed state, shown in FIG. 31A, the narrow portion of the elongated ribs are engaged within the U-shaped regions in the lockout tabs, thereby providing more play which allows for easier deployment. As the stent expands, however, the ladder elements slide open and the ribs widen, thereby reducing play and insuring better tab engagement in the now wider slots.

The ladder elements on either end of the low-profile stent are designed to be fully supported radially by attaching to the bottom instead of the top of the target element to complete the ring. When assembling the stent, individual series of nesting ladder elements that form a complete ring, are rolled separately. The elongated ribs 108 and 110 are bowed to define a circumferential arc of a tubular member that is formed when the series is rolled. Multiple tubular series, each comprising about 3–8 nested ladder elements, are then attached together to get the stent length desired. This configuration is both more flexible in delivery and when expanded that stent designs that use short articulations to connect crowns. These articulations may become work-hardened and eventually fracture during long-term implantation. Such problems are minimized in this low-profile embodiment by using flexible string-steel materials.

The series may be rolled between two plates, which are each padded on the side in contact with the stent elements. One plate is held immobile and the other can move laterally with respect to the other. Thus, the stent elements sandwiched between the plates may be rolled about a mandrel by the movement of the plates relative to one another. Alternatively, 3-way spindle methods known in the art may be used to roll the series.

The individual ladder elements may be die-cut or chemically etched. Chemical etching provides high-resolution components at relatively low price, particularly in comparison to cost of competitive product laser cutting. Tack-welding may be used to attach the cross-ties on metal components. Where plastic and/or bioabsorbable materials are used, the elements may be made using hot-stamp embossing to generate the parts and heat-staking to attach the cross-ties.

In addition to the metal alloys described above, the low-profile embodiment of the expandable stent may also be made from biodegradable materials in order that the stent may be absorbed after it has served its usefulness. Generally, the usefulness of a stent past 2–4 months is questionable. Indeed, "instent" restenosis is difficult to treat. Biodegradable materials may include polypeptides, polydepsipeptides, nylon copolymides, aliphatic polyesters, such as polyglycolic acid (PGA), polylactic acid (PLA), polyalkylene succinates, polyhydroxybutyrate (PHB), polybutylene diglycolate, and poly e-caprolactone (PCL), polydihydropyrans, polyphosphazenes, polyorthoesters, polycyanoacrylates, and their chemical modifications and combinations and many other biodegradable materials known in the art (See e.g., Atala, A., Mooney, D. Synthetic Biodegradable Polymer Scaffolds. 1997 Birkhauser, Boston.; incorporated herein by reference).

Soluble materials such as hydrogels which are hydrolized by water in blood could also be used. Cross-linked poly 2-hydroxyethyl methacrylate (PHEMA) and its copolymers, e.g., polyacrylamide, and polyvinyl alcohol.

Drugs and other bioactive compounds could be incorporated into the biodegradable matrices and thereby provide sustained release of such compounds at the site of the stenosis. The list of examples for coating stents made from metal and/or other nonbiodegradable materials above, could also be used for incorporation into biodegradable stents.

Figure 32:
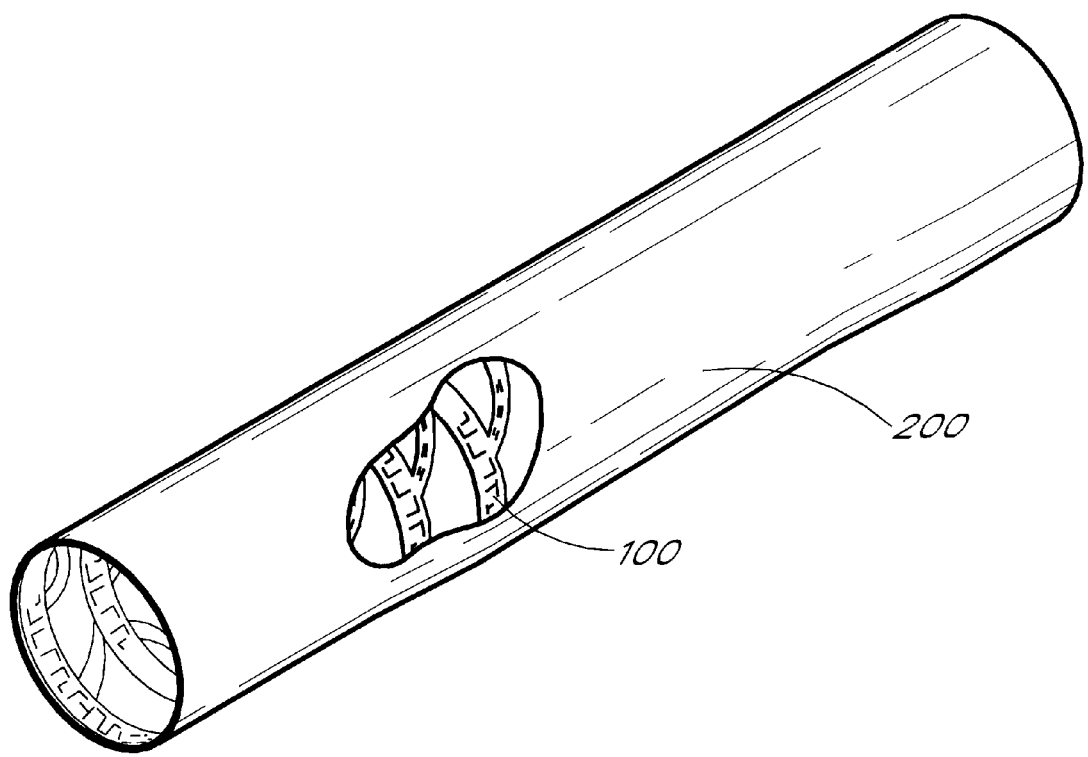
FIG. 32 is a perspective view of an embodiment of the present invention showing a stent having a sheath.

The low-profile stents in accordance with the embodiment illustrated in FIGS. 30 and 31 may also be useful in vessel grafts, wherein the stent is covered with a sheath formed from either a polymeric material, such as expanded PTFE, or a natural material, such as fibrin. One variation of a graft in accordance with the present invention is illustrated in FIG. 32. The tubular graft comprises a low profile expandable stent 100 and a polymeric sheath 200. Furthermore, because of the very low profile, small collapsed diameter and great flexibility, stents made in accordance with this embodiment may be able to navigate small or torturous paths. Thus, the low-profile variation may be useful in coronary arteries, carotid arteries, vascular aneurysms (when covered with a sheath), renal arteries, peripheral (iliac, femoral, popliteal, subclavian) arteries. Other nonvascular applications include gastrointestinal, duodenum, biliary ducts, esophagus, urethra, tracheal and bronchial ducts.

While a number of preferred embodiments of the invention and variations thereof have been described in detail, other modifications and methods of using and medical applications for the same will be apparent to those of skill in the art. Accordingly, it should be understood that various applications, modifications, and substitutions may be made of equivalents without departing from the spirit of the invention or the scope of the claims.

What is claimed is:

1. An expandable intraluminal stent comprising:
   a tubular member comprising a series of slideably engaged ladder elements, each ladder element comprising at least two radially disposed elongated ribs, each having two ends, and at least two end rungs, wherein an end rung is permanently, non-slideably affixed to each end of each elongated rib, such that each of said ribs has no protruding ends when said tubular member is in either a first collapsed diameter or a second expanded diameter;
   wherein an elongated rib from a first ladder element is slidably engaged by a portion of an end rung from a second ladder element, such that radial sliding of the ladder elements creates a variable radial distance between the end rungs of the first and second ladder elements;
   said tubular member having said first diameter in which the distance between end rungs of the first and second ladder elements is collapsed; and
   said tubular member having said second diameter in which the distance between end rungs of the first and second ladder elements is expanded.

2. The expandable stent of claim 1, wherein at least one elongated rib on each ladder element has a plurality of slots adapted to engage a lockout tab on the end rung of an adjacent ladder element.

3. The expandable stent of claim 2, wherein said slots and lockout tabs permit the end rungs to slide apart, thereby expanding the diameter of the tubular member, but wherein said lockout tabs engage said slots to prevent the end rungs from sliding back toward a more collapsed state.

4. The expandable stent of claim 1, wherein said tubular member expands from the first, collapsed diameter to the second, expanded diameter upon application from inside the tubular member of a radially outwardly extending force.

5. The expandable stent of claim 1, wherein said tubular member self-expands to the second, expanded diameter upon the removal of a restraint which holds the tubular member in the first, collapsed diameter.

6. The expandable stent of claim 1, wherein the ladder elements are made from an alloy selected from the group consisting of stainless steel, elgiloy, tantalum, titanium and Nitinol.

7. The expandable stent of claim 1, wherein the ladder elements are made from at least one biodegradable material selected from the group consisting of polypeptides, polydepsipeptides, nylon copolymides, aliphatic polyesters, polydihydropyrans, polyphosphazenes, polyorthoesters, polycyanoacrylates, and their derivatives.

8. The expandable stent of claim 7, wherein a bioactive agent is incorporated into the biodegradable material, said bioactive material being selected from the group consisting of heparin, hirudin, warfarin, ticlopidine, dipyridarnole, GPIIb/IIIa receptor blockers, thromboxane inhibitors, serotonin antagonists, prostanoids, calcium channel blockers, PDGF antagonists, ACE inhibitors, angiopeptin, enoxaparin, colchicine, steroids, non-steroidal anti-inflammatory drugs, VEGF, adenovirus, enzymes, sterol, hydroxylase, antisense sequences, fish oils, HMG, Co-A reductase inhibitors, ibutilide fumarate, adenylcyclase, growth factors, nitric oxide, proteins, peptides and carbohydrates.

9. The expandable stent of claim 1, wherein at least a portion of the stent is radiopaque.

10. The expandable stent of claim 1, wherein the stent may have a wall thickness in a range from about 0.01 to about 0.0001 inches.

11. The expandable stent of claim 1, wherein the stent may have a wall thickness of less than about 0.0007 inches.

12. The expandable stent of claim 1, wherein at a width of the elongated ribs increase progressively from a narrow end to a wide end.

13. The expandable stent of claim 1, wherein the tubular member further comprises a sheath.

* * * * *